(12) United States Patent
Wilhelm et al.

(10) Patent No.: US 12,162,804 B2
(45) Date of Patent: Dec. 10, 2024

(54) SINTERING PROCESS FOR ELECTRICAL FEEDTHROUGHS

(71) Applicant: Heraeus Deutschland Gmbh & Co. KG, Hanau (DE)

(72) Inventors: Leoni Wilhelm, Hanau (DE); Ulrich Hausch, Hanau (DE); Robert Dittmer, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 414 days.

(21) Appl. No.: 17/346,380

(22) Filed: Jun. 14, 2021

(65) Prior Publication Data

US 2021/0403388 A1 Dec. 30, 2021

(30) Foreign Application Priority Data

Jun. 25, 2020 (DE) ............... 10 2020 116 805.5

(51) Int. Cl.
| | |
|---|---|
| *C04B 35/111* | (2006.01) |
| *A61N 1/375* | (2006.01) |
| *B22F 3/10* | (2006.01) |
| *C04B 35/64* | (2006.01) |
| *H05K 5/02* | (2006.01) |

(52) U.S. Cl.
CPC .......... *C04B 35/111* (2013.01); *A61N 1/3754* (2013.01); *B22F 3/1017* (2013.01); *C04B 35/64* (2013.01); *H05K 5/0247* (2013.01); *C04B 2235/3206* (2013.01); *C04B 2235/3217* (2013.01); *C04B 2235/3244* (2013.01); *C04B 2235/6562* (2013.01); *C04B 2235/6581* (2013.01); *C04B 2235/6583* (2013.01); *C04B 2235/6588* (2013.01); *C04B 2235/661* (2013.01)

(58) Field of Classification Search
CPC .................................... C04B 35/111
See application file for complete search history.

(56) References Cited

U.S. PATENT DOCUMENTS

| | | | |
|---|---|---|---|
| 4,225,344 | A | 9/1980 | Fujimori et al. |
| 4,921,822 | A | 5/1990 | Luthra |
| 6,997,071 | B2 | 2/2006 | Jiang et al. |

(Continued)

FOREIGN PATENT DOCUMENTS

| | | |
|---|---|---|
| DE | 2831293 | 2/1979 |
| DE | 3786163 | 1/1994 |

(Continued)

OTHER PUBLICATIONS

Karbasi, Ali, "Developing a High Density Pt/Alumina Hermetic Feedthrough" (2012) FIU Electronic Theses and Dissertations 667 https://digitalcommons.fiu.edu/etd/667.*

(Continued)

*Primary Examiner* — Christopher S Kessler
(74) *Attorney, Agent, or Firm* — Dicke, Billig & Czaja, PLLC (57) ABSTRACT

One aspect relates to a process for producing a sintered workpiece, which includes sintering of a ceramic material at a temperature of at least 1000° C. and in an atmosphere, in the case of which the partial pressure of atmospheric air is reduced to less than $10^{-6}$-times, based on the ambient air at the same temperature under equilibrium conditions.

12 Claims, 3 Drawing Sheets

(56) References Cited

U.S. PATENT DOCUMENTS

| | | | |
|---|---|---|---|
| 10,212,836 B2 | 2/2019 | Dittmer et al. | |
| 10,290,400 B2 | 5/2019 | Troetzschel et al. | |
| 10,969,670 B2 | 4/2021 | Ronda et al. | |
| 2007/0158446 A1 | 7/2007 | Wang et al. | |
| 2008/0060834 A1 | 3/2008 | Eck et al. | |
| 2010/0294419 A1* | 11/2010 | Feltz | H10N 30/053 156/89.12 |
| 2011/0125210 A1 | 5/2011 | Francis et al. | |
| 2012/0193125 A1 | 8/2012 | Pavlovic et al. | |
| 2012/0197335 A1 | 8/2012 | Reisinger | |
| 2015/0137404 A1* | 5/2015 | Tuchinskiy | B22F 7/06 264/642 |
| 2017/0291033 A1 | 10/2017 | Dittmer et al. | |
| 2018/0362409 A1 | 12/2018 | Watanabe | |

FOREIGN PATENT DOCUMENTS

| | | |
|---|---|---|
| DE | 69729719 | 7/2005 |
| DE | 10 2009 035 972 | 4/2011 |
| DE | 10 2011 009 858 | 8/2012 |
| EP | 1514578 | 3/2005 |
| EP | 1897588 | 3/2008 |
| EP | 3224674 | 10/2017 |
| EP | 3351290 | 7/2018 |
| EP | 3388406 | 10/2018 |
| GB | 2081741 | 2/1982 |
| WO | 2011/065989 | 6/2011 |
| WO | 2017/068153 | 4/2017 |

OTHER PUBLICATIONS

Kelly Direct Bonding of Mo and Nb Feedthroughs in Electronic-Grade Al2O3 Ceramic Engineering and Science Proceedings, vol. 3 (1982), Issue 9/10.

Mata-Osoro; Moya; Pecharroman Transparent alumina by vacuum sintering Journal of the European Ceramic Society 32, Mar. 23, 2012, 2925-2933.

* cited by examiner

SINTERING PROCESS FOR ELECTRICAL FEEDTHROUGHS

CROSS-REFERENCE TO RELATED APPLICATION

This Utility Patent application claims priority to German Application No. 10 2020 116 805.5 filed on Jun. 25, 2020, which is incorporated herein by reference.

TECHNICAL FIELD

One embodiment relates to the field of material technology, in one embodiment the production of ceramic products, for example a cermet-containing electrical feedthrough for use in the medical technology.

BACKGROUND

DE 697 297 19 T2 describes an electrical feedthrough for an active, implantable medical device—also referred to as implantable device or therapy device. Electrical feedthroughs of this type serve the purpose of establishing an electrical connection between a hermetically sealed interior and an exterior of the therapy device. The hermetic tightness with respect to a surrounding area is an essential requirement for an electrical feedthrough. Conduit elements, which are introduced into an electrically insulating base body and via which the electrical signals run, therefore have to be introduced into the insulating base body in a gap-free manner. It turned out to be advantageous thereby to design the conduit elements as cermet. Cermets are composite materials made of powdery metal and one or several ceramics. Cermets make it possible to establish a direct substance-to-substance bond between the conduit element and the surrounding insulating ceramic base body of the feedthrough by using co-sintering. If massive metallic conduit wires are used instead of cermets, they have to be introduced into the ceramic in complex processes, in order to create a hermetically tight connection. For the medical use of implantable medical devices, it is necessary to attain a highest possible quality with respect to this hermetic tightness.

Processes for sintering ceramics and/or cermets are known in the prior art, which usually take place in an uncontrolled gas composition, i.e. in ordinary room air. This means that the gas atmosphere, which directly surrounds the workpiece during the sintering, is usually essentially identical to the composition of the atmosphere, which is located outside of the sintering device. In addition, it is common to carry out such processes at increased pressure, in order to support the sintering process. One example of such a process is described in EP 3 351 290 A1. It is proposed there to carry out the process at normal pressure or elevated pressure of, for example, up to at least 1000 bar. Due to the fact that, as is well known, commonly used ceramic materials, such as $Al_2O_3$ and components of cermets, such as, for example, platinum, are inert even at high temperatures, there was no reason so far in the prior art to carry out the sintering process in a controlled gas atmosphere.

For these and other reasons there is a need for the present embodiment.

SUMMARY

An object of one embodiment is to solve one or several of the above-described and further problems of the prior art. For example, one embodiment provides for an improved production process for producing a ceramic workpiece, for example a cermet-containing electrical feedthrough. One embodiment furthermore provides ceramic workpieces with improved properties.

These objects are solved by using the processes and devices described herein, in particular those, which are described in the patent claims.

Exemplary embodiments are described below.

1. A process for producing a sintered workpiece, comprising sintering of a ceramic material at a temperature of at least 1000° C. and in an atmosphere, in the case of which the partial pressure of atmospheric air is reduced to less than $10^{-6}$-times (i.e. 10E-6 times), preferably less than $10^{-7}$-times (i.e. 10E-7 times) or less than $10^{-8}$-times (i.e. 10E-8 times), based on the ambient air at the same temperature under equilibrium conditions.
2. The process according to embodiment 1, wherein the atmosphere during the sintering has a total pressure of less than 100 Pa, preferably less than 50; 10; 5; 1; 0.5; 0.1; 0.01, or less than 0.001 Pa.
3. The process according to embodiment 1 or 2, wherein the atmosphere during the sintering has a partial oxygen pressure of less than 1 Pa, preferably less than 0.5; 0.1; 0.01, or less than 0.001 Pa.
4. The process according to any one of the preceding embodiments, wherein the atmosphere during the sintering has a partial water pressure of less than 1 Pa, preferably less than 0.5; 0.1; 0.01, or less than 0.001 Pa.
5. The process according to any one of the preceding embodiments, further comprising pre-sintering of the ceramic material at a temperature of at least 400° C., preferably 800° C., or more than 1000° C.
6. The process according to any one of the preceding embodiments, wherein the workpiece is heated maximally for 6 hours, preferably maximally for 3 hours, or maximally for 1 hour to a temperature of more than 1500° C., preferably more than 1600° C.
7. The process according to any one of the preceding embodiments, wherein the atmosphere comprises a protective gas, preferably argon, or nitrogen, helium, or a combination thereof, or essentially consists thereof.
8. The process according to any one of the preceding embodiments, wherein the ceramic material comprises a metal oxide, preferably a metal oxide selected from the group consisting of alumina ($Al_2O_3$), magnesia (MgO), zirconia ($ZrO_2$), aluminum titanate ($Al_2TiO_5$), and piezoceramics, more preferably selected from the group consisting of alumina and zirconia, or a combination thereof.
9. The process according to any one of the preceding embodiments, wherein the ceramic material comprises a cermet.
10. The process according to embodiment 9, wherein the cermet comprises a precious metal, wherein the precious metal is preferably selected from the group consisting of platinum, silver, gold, tantalum, molybdenum, and titanium.
11. The process according to any one of the preceding embodiments, wherein the workpiece is suitable for installation in an implantable medical product, wherein the medical product is preferably selected from the group consisting of a pulse generator, pacemaker, cardiac resynchronization device, actuator, sensor, or stimulator.
12. A sintered workpiece, produced according to a process according to any one of the preceding embodiments.

13. A sintered workpiece, comprising a plane of a sintered material made of ceramic or cermet, wherein the plane
(a) is essentially free from cracks with a width of more than 10 nm; or
(b) comprises cracks, wherein at least 95%, 96%, 97%, 98%, or at least 99% of the cracks have a width of less than 10 nm.
14. A sintered workpiece, comprising a ceramic and a cermet, wherein the ceramic and the cermet form boundary surfaces with one another, wherein the boundary surfaces are essentially free from cracks with a width of more than 10 nm.
15. The sintered workpiece according to any one of embodiments 12 to 14, which has a helium leak rate of less than $10^{-7}$ (10E-7), $10^{-8}$ (10E-8), $10^{-9}$ (10E-9), $10^{-10}$ (10E-10), or $10^{-11}$ (10E-11) atm*cm$^3$/s.
16. The sintered workpiece according to any one of embodiments 12 to 15, which is an electrical feedthrough for an implantable medical device.
17. The sintered workpiece according to any one of embodiments 12 to 16, which has a helium leak rate of less than $10^{-11}$ atm*cm$^3$/s after more than 3 months, or preferably more than 6 months, after the production.
18. The sintered workpiece according to any one of embodiments 12 to 17, comprising a sintered ceramic material, which has a porosity of less than 1% by volume.
19. A sintered workpiece, comprising a sintered ceramic material, which has an average grain at least 5 μm.
20. A sintered workpiece comprising a sintered ceramic material, which has an average grain size of at least 10 μm.
21. A sintered workpiece, comprising a sintered ceramic material, which has a porosity of less than 1.5%, preferably less than 1.2%, 1.0%, 0.8%, 0.6%, or 0.5% by volume.
22. The sintered workpiece according to any one of embodiments 12, 13, or 15 to 21, comprising a ceramic material and a cermet.
23. The sintered workpiece according to any one of embodiments 12 to 21, which is an electrical feedthrough for installation in a medical device.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the embodiment may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiment. The following detailed description, therefore, is not to be taken in a limiting sense, and the scope of the present embodiment is defined by the appended claims.

It is to be understood that the features of the various exemplary embodiments described herein may be combined with each other, unless specifically noted otherwise.

In addition to the embodiments described herein, the elements of which "have" or "comprise" a certain feature (e.g. a material), a further embodiment is generally always considered, in which the respective element consists solely of the feature, i.e. does not include any further components. The word "comprise" or "comprising" is used synonymously with the word "have" or "having" herein.

When an element is identified in the singular form in an embodiment, an embodiment is likewise considered, in the case of which several of these elements are present. The use of a term for an element in the plural form generally also includes an embodiment, in which only an individual corresponding element is included.

Unless otherwise specified or excluded unambiguously from the context, it is generally possible and is hereby unambiguously considered that features of different embodiments can also be present in the other embodiments described herein. It is likewise generally considered that all features, which are described herein in connection with a process, can also be used for the products and devices described herein, and vice versa. All of these considered combinations are not listed explicitly in all cases only in the interest of a more concise description. Technical solutions, which are obviously equivalent to the features described herein, are to generally be included by the scope.

One aspect of one embodiment relates to a process for producing a sintered workpiece, comprising sintering of a ceramic material at a temperature of at least 1000° C. and in an atmosphere, in the case of which the partial pressure of atmospheric air is reduced to less than $10^{-6}$-times, compared to the pressure of ambient air at the same temperature under equilibrium conditions.

According to one embodiment, the above-mentioned temperature is the temperature of the atmosphere, which surrounds the ceramic material. It is assumed that this temperature is essentially identical to the temperature of the ceramic material because the process is generally carried out such that the ceramic material and the atmosphere are largely in thermal equilibrium with one another.

The same applies for the further temperature values specified herein during the process, which are described herein below.

In the case of the described process, the partial pressure of atmospheric air is reduced to less than $10^{-6}$-times, based on the ambient air at the same temperature under equilibrium conditions. This means that the process is carried out in an enclosed room, from which the original gas atmosphere is largely removed. This can take place by pumping out the original gas atmosphere, usually the atmospheric room air. Either the total pressure in the closed room can thereby be lowered during the sintering, or the atmospheric room air can be replaced by a different gas. In these two described cases, it is significant for the process that the originally present room air is removed from the room, so that maximally $10^{-6}$-times the portion of the originally present gas atmosphere remains in the closed room, in which the sintering process takes place subsequently. For this purpose, the originally present atmosphere can be pumped out, until the pressure, measured by using a manometer, is less than $10^{-6}$-times the initial pressure, for example less than 0.1 Pa. The measurement of the pressure thereby takes place before and after the pump-out at the same temperature, for example 25° C. The original gas atmosphere is in one embodiment removed from the closed room at normal room temperature, for example approximately 20 to 25° C., before the ceramic material is sintered at a significantly higher temperature of at least 1000° C. The ceramic material can be sintered, for example, at approximately 1500° C., 1600° C., or 1700° C. In one embodiment, the ceramic material is sintered at a temperature of from 1400° C. to 1800° C., in one embodiment 1500° C. to 1700° C.

The partial pressure of atmospheric air is in one embodiment reduced to $10^{-7}$-times or less than $10^{-8}$-times, based on the ambient air at the same temperature under equilibrium conditions.

As common in the technical field, sintering herein describes the connection of particles by using heating. A fixed cohesive workpiece can thereby be created, for example from a ceramic paste.

When the removed atmospheric air is not replaced by a different gas, the sintering process is carried out at lowered pressure, so that the atmosphere during the sintering, i.e. after the heating of the ceramic material to at least 1000° C., has a total pressure of less than 100 Pa, in one embodiment less than 50; 10; 5; 1; 0.5; 0.1; 0.01, or less than 0.001 Pa. In this case, the pressure refers to the total pressure of the atmosphere of the gas, which directly surrounds the ceramic material, during the sintering process, for example at 1000° C. or more.

The partial oxygen pressure of the gas, which directly surrounds the ceramic material, during the sintering process, for example at 1000° C. or more, can be, for example, less than 1 Pa, in one embodiment less than 0.5; 0.1; 0.01, or less than 0.001 Pa.

The temperature of the gas atmosphere during the sintering can be, for example, approximately 1000° C., approximately 1050° C., approximately 1100° C., approximately 1150° C., approximately 1200° C., approximately 1250° C., or approximately 1300° C., 1350° C., 1400° C., 1450° C., or approximately 1500° C. In some embodiments, the temperature during the sintering is approximately 1500° C. or higher, or approximately 1600° C. or higher. The exact temperature during the sintering can be selected and adapted as a function of the used materials.

The heating of the ceramic material can take place with a heating rate of at least 200, 300, 400, or more than 400 K/h, for example 450 or 500 K/h.

In one embodiment, the sintering process takes place with a decreased water content of the gas atmosphere. The atmosphere during the sintering can have, for example, a partial water pressure of less than 1 Pa, in one embodiment less than 0.5; 0.1; 0.01, or less than 0.001 Pa, measured at the used sintering temperature, for example at 1000° C.

The ceramic material can include a binding agent. The binding agent can include an organic polymer. An alkyl cellulose, such as, for example, methyl cellulose or ethyl cellulose, is an example for a suitable binding agent. The ceramic material can furthermore include a solvent. By adding the binding agent and optionally the solvent, a paste can be produced from a ceramic powder, which can be formed into a so-called green body or a green body film. Prior to the sintering, several green body films can optionally be formed into a laminate and can be firmly connected to one another under pressure, for example isostatic pressing. Prior to the sintering, i.e. prior to the heating to a temperature of at least 1000° C., the process can additionally include a step, in which the binding agent is removed by heating the ceramic material. In the technical field, this is also referred to as debinding. In the cases, in which the process includes a below-described pre-sintering step, the debinding can be performed prior to this pre-sintering step. The debinding includes, for example, the heating of the ceramic material to more than 300° C., more than 350° C., more than 400° C., or more than 450° C. for several hours, for example, more than one, more than 2, more than 3, more than 4, or more than 5 hours. The heating of the ceramic material can take place at a heating rate of at least 50, 60, 70, 80, 90, or 100 K/h.

Prior to the sintering, thus prior to the heating to a temperature of at least 1000° C., the process can additionally include a step, in the case of which the ceramic material is pre-sintered at a temperature of at least 400° C. This step is also referred to herein as pre-sintering step and can be performed in ordinary room air, thus before the partial pressure of atmospheric air is reduced, as described above. The step can also be performed after the partial pressure of the atmospheric air is reduced. In the case of this step, the temperature of the gas atmosphere can be increased, for example, to 500° C., 600° C., 700° C., or 800° C. The ceramic material can also be pre-sintered, for example, at least 1000° C. or at least 1100° C., and can subsequently be sintered at an even higher temperature. The used temperatures can be adapted, depending on the type and nature of the ceramic material. For example in the case of different materials or different particle sizes, different temperatures can be advantageous in each case. The pre-sintering step can take place at a heating rate of at least 200, 300, 400, or more than 400 K/h, for example 450 or 500 K/h.

In some embodiments, the workpiece for sintering is heated to a temperature of more than 1500° C. or more than 1600° C. for the shortest possible period, for example maximally 6 hours. For example, the workpiece is heated to a temperature of more than 1500° C., in one embodiment more than 1600° C., for maximally 3 hours or maximally 1 hour. The mentioned temperature is in each case determined with reference to the gas atmosphere surrounding the workpiece, whereby it is generally assumed that the ceramic material and the surrounding gas atmosphere are essentially in thermal equilibrium with one another, as already described herein. The duration of the process can be shorted by sintering at a higher temperature, so that the production of the workpiece can take place more cost-efficiently, without impacting the high quality, for example tightness, of the produced sintered workpiece.

In one embodiment, the process can be carried out, for example, as follows:
1. debinding the ceramic material in normal room air at 450° C. for 5 hours, whereby the ceramic material is first heated at a heating rate of 90K/h to 450° C.;
2. pre-sintering the ceramic material in normal room air at 1100° C. for 1 hour, whereby the ceramic material is first heated at a heating rate of 450K/h to 1100° C.;

3. sintering the ceramic material under vacuum or argon atmosphere at 1650° C. for 3 hours, whereby the ceramic material is first heated at a heating rate of 450K/h to 1650° C.;
4. grinding the sintered workpiece to the desired thickness;
5. cutting out the desired structure and mechanical machining to the desired final geometry.

In some embodiments, a protective gas is introduced after pumping out the original gas atmosphere, so that a total pressure of, for example, approximately 100.000 kPa or approximately 1 atm, is reestablished in the closed room, in which the ceramic is located during the sintering. The original gas atmosphere is thereby essentially replaced by the protective gas, so that the subsequent sintering process takes place under protective gas atmosphere. Noble gases, for example argon or helium, or purified nitrogen, are examples for suitable protective gases. The protective gas can also include a combination of the mentioned gases. In one embodiment, the protective gas is synthetic air (80% by volume of nitrogen, 20% by volume of oxygen).

A ceramic material is in one embodiment selected from the group consisting of an oxide ceramic, a silicate ceramic, a non-oxide ceramic, and an element ceramic, or a mixture of at least two of them.

The oxide ceramic is in one embodiment selected from the group consisting of a metal oxide, a semi-metal oxide, or a mixture thereof. The metal of the metal oxide can be selected from the group consisting of aluminum, beryllium, barium, calcium, magnesium, sodium, potassium, iron, zirconium, titanium, or a mixture of at least two of them. The metal oxide is in one embodiment selected from the group consisting of alumina ($Al_2O_3$), magnesia (MgO), zirconia ($ZrO_2$), yttria ($Y_2O_3$), aluminum titanate ($Al_2TiO_5$), a piezo-ceramic, such as lead zirconate ($PbZrO_3$), lead titanate ($PbTiO_3$), as well as lead zirconate titanate (PZT), or a mixture of at least two of them. The semi-metal of the semi-metal oxide is in one embodiment selected from the group consisting or boron, silicon, arsenic, tellurium, or a mixture of at least two of them. A further preferred oxide ceramic is in one embodiment selected from the group consisting of zirconia toughened alumina (ZTA—$Al_2O_3$/$ZrO_2$), yttrium toughened zirconia (Y-TZP), barium (Zr, Ti) oxide, barium (Ce, Ti) oxide, or a combination of at least two of them.

The silicate ceramic is in one embodiment selected from the group consisting of a steatite ($Mg_3[Si_4O_{10}](OH)_2$]), cordierite ($(Mg, Fe^{2+})_2 (Al_2Si)[Al_2Si_4O_{18}]$), mullite ($Al_2Al_{2+2x}Si_{2-2x}O_{10-x}$ with x=oxygen vacancies per elementary cell), feldspar ($Ba,Ca,Na,K,NH_4)(Al,B,Si)_4O_8$), or a mixture of at least two of them.

The non-oxide ceramic can be selected from the group consisting of a carbide, a nitride, or a mixture thereof. The carbide can be selected from the group consisting of silicon carbide (SiC), boron carbide ($B_4C$), titanium carbide (TiC), tungsten carbide, cementite (Fe3C). The nitride can be selected from the group consisting of silicon nitride ($Si_3N_4$), aluminum nitride (AlN), titanium nitride (TiN), silicon aluminum oxynitride (SIALON), or a mixture of at least two of them. Sodium-potassium-niobate is a further preferred non-oxide ceramic.

The element ceramic is in one embodiment carbon, in one embodiment diamond. A diamond powder is preferred in one embodiment mixed with a metal powder in order to produce a cermet, which contains an element ceramic as ceramic component. Such a cermet with an element ceramic as ceramic component is characterized by a particularly preferred combination of high hardness and high specific heat conductivity.

In one embodiment, the ceramic material includes a metal oxide, in one embodiment a metal oxide selected from the group consisting of alumina (Al2O3), magnesia (MgO), zirconia (ZrO2), aluminum titanate (Al2TiO5), and piezoceramics, in one embodiment selected from the group consisting of alumina and zirconia, or a combination thereof.

In one embodiment, the ceramic material includes a cermet. A composite material of a ceramic and a metal is referred to as "cermet". For example, a mixture of at least one ceramic powder and at least one metallic powder can be used to produce a cermet. At least one binding agent and optionally at least one solvent can be added to this mixture, in order to obtain a malleable green body. Afterwards, the binding agent and optionally the solvent are completely removed thermally or by using evaporation during the so-called debinding. All substances, which are mentioned as ceramic materials further above herein, are generally suitable substances for the ceramic contained in the cermet.

The cermet can be electrically conductive. An electrically conductive connection generally sets in in the cermet when the metal content lies above the so-called percolation threshold, at which the metal particles in the sintered cermet are connected to one another at least pointwise, so that an electrical conduction is made possible. According to experience, the metal content can for this purpose be, for example, at least 25% by volume, depending on the material selection.

The cermet can include a precious metal. The precious metal is in one embodiment selected from the group consisting of platinum, silver, gold, tantalum, molybdenum, and titanium.

The process can in one embodiment be completely or partially carried out in a tool or a mold, or both, so that a shaping can be connected to the sintering process. In addition to powdery materials, a starting material for the sintering process can include further materials, for example one or several binding agents or one or several solvents, or both. The sintering process can take place in one step or also in several steps, wherein the sintering process can be preceded, for example, by further steps, for example one or several shaping steps, or one or several debinding steps, or both. The sintering process, in one embodiment for a cermet, can run similarly to steps to a sintering process, which is usually used for homogenous powders. The material can be compressed during the sintering process, for example at a high temperature, so that the cermet is virtually tight, or has a maximally closed porosity. Cermets are often characterized by a particularly high hardness and wear resistance.

The process can furthermore include the grinding of the workpiece after the sintering and cool-down. The workpiece can be ground down, for example, by using silicon carbide sandpaper (grain size: 2400). The process can furthermore include the deburring of the workpiece. The grinding and/or deburring can lead to a smoother surface and/or improved stability of the workpiece.

The process can include a HTCC (high-temperature cofired ceramic) process, as it is known from the field of electronics manufacturing. Examples of such processes are described in EP3351290B1, WO2011065989A1, and Barlow/Elshabini: Ceramic Interconnect Technology Handbook, CRC Press, 2007; which are hereby incorporated completely by reference.

For example, an electrical feedthrough, which includes a conduit element, which has a cermet, can be produced by using the process described herein. For example, such a feedthrough can be produced as follows: At first, a green body film can be made available and can be provided with holes, for example by using punching. The holes can be filled with a suitable cermet paste. At this stage of the production, the cermet paste can include at least a mixture of metal powder, ceramic powder, and an organic vehicle. Several of the green body films filled in this way can subsequently be laminated, so that the cermet-filled holes are arranged one on top of the other. They can subsequently form the conduit element. So many filled green body films can be laminated that the desired thickness of the electrical feedthrough or length of the conduit element, respectively, is reached. During the subsequent firing, the organic vehicle can be removed at first, the cermet and the ceramic base body can be co-sintered during the subsequent transition to higher temperatures. In one embodiment a hermetically tight substance-to-substance bond between the ceramic component of the cermet and the surrounding ceramic of the base body can be created thereby.

A further embodiment is the use of a process described herein for producing a sintered workpiece, for example an implantable medical product, or of a portion thereof, for example an electrical feedthrough.

In a further aspect of one embodiment includes a sintered workpiece, which can be or is produced according to a process described herein.

The workpiece produced by using the process described herein can be suitable or intended, for example, for installation in an implantable medical product. The medical product is selected, for example, from the group consisting of a pulse generator, medical electrode, pacemaker, cardiac synchronization device, actuator, sensor, or stimulator. The workpiece can be, for example, an electrical feedthrough for an implantable medical device.

In one embodiment, the workpiece is a sensor or a lamp, for example a deuterium lamp, or an LED.

A pulse generator can be set up, for example, to provide an electrical signal for a medical electrode or stimulator. Such a medical electrode or stimulator can be set up, for example, for the stimulation of human tissue, for example muscle tissue (including heart), nerve tissue (including brain), or tissue of the digestive tract.

The sintered workpieces, which are produced by using the processes described herein, are in one embodiment characterized in that the essentially do not have any microcracks, and thus have a particularly high tightness.

The sintered workpiece can be essentially free from cracks. For example, essentially no cracks with a width of more than 10 nm are present in the sintered workpiece. In one embodiment, at least 95%, 96%, 97%, 98%, or at least 99% of the cracks in the sintered workpiece have a width of less than 10 nm. This can take place by analysis of the surface of the workpiece or of an exposed cross-sectional surface of the workpiece by using a suitable measuring procedure, for example electron microscopy or atomic force microscopy. This inner cross sectional surface of the workpiece can be exposed, for example, by using water jet cutting, as described in Ordung et al., Laser Cutting and Joining of 2D-Reinforced CMC, in: Ceramic Materials and Components for Engines, Wiley-VCH, DOI: 10.1002/9783527612765.c107, ISBN: 9783527612765.

In one embodiment, the workpiece includes a ceramic and a cermet, wherein the ceramic and the cermet form boundary surfaces with one another. The boundary surfaces of the workpiece are thereby essentially free from cracks, in one embodiment essentially free from cracks with a width of more than 10 nm. This can be at hand, for example, when essentially no cracks can be determined along the boundary surface between ceramic and cermet in an electron micrographic picture of an exposed cross-sectional plane of the sintered workpiece.

These sintered workpieces can have a particularly high tightness. For example, the sintered workpiece can have a helium leak rate of less than $10^{-7}$ atm*cm$^3$/s. A sintered workpiece, for example an electrical feedthrough, with such a helium leak rate can be referred to as "hermetically tight". In one embodiment, the sintered workpiece has a helium leak rate of less than $5 \times 10^{-8}$ atm*cm$^3$/s, or less than $10^{-9}$, $10^{-10}$, or $10^{-11}$ atm*cm$^3$/s. In one embodiment, the sintered workpiece has a helium leak rate of less than $10^{-7}$, $10^{-8}$, $10^{-9}$, $10^{-10}$, or less than $10^{-11}$ mbar/L·s.

The term "hermetically tight" clarifies that moisture and/or gases cannot permeate or can only minimally permeate through the hermetically tight element in the case of a proper use within the usual time periods (for example 5-10 years). A physical variable, which can describe, for example, a permeation of gases and/or moisture through a device, e.g. through the electrical feedthrough, is the so-called leak rate, which can be determined, for example, by using leak tests. Corresponding leak tests can be performed, for example, with helium leak testers and are specified in the standard Mil-STD-883G Method 1014. The maximally permissible helium leak rate is thereby specified as a function of the internal volume of the device to be tested. According to the methods specified in MIL-STD-883G, Method 1014, in paragraph 3.1, and in consideration of the volumes occurring when using the present embodiment and cavities of the devices to be tested, these maximally permissible helium leak rates can be, for example, between $1 \times 10^{-8}$ atm. cm$^3$/sec and $1 \times 10^{-7}$ atm. cm$^3$/sec. In the context of one embodiment, the term "hermetically tight" can in one embodiment mean that the workpiece to be tested, in one embodiment an electrical feedthrough, has a helium leak rate of less than $1 \times 10^{-7}$ atm. cm$^3$/sec. In an advantageous embodiment, the helium leak rate can be less than $10^{-8}$, $10^{-9}$, $10^{-10}$, or less than $10^{-11}$ mbar/L·s. For the purpose of the standardization, the mentioned helium leak rates can also be converted into the equivalent standard air leak rate. The definition for the equivalent standard air leak rate and the conversion are specified in the standard ISO 3530.

The workpieces produced according to the process according to one embodiment can have a number of advantages, for example have a high mechanical and/or thermal capacity compared to conventional processes. The produced workpieces can have a particularly low porosity. In the cases, in which the workpiece is made from several green body films, the delamination of these individual layers can be reduced or prevented by using the process according to one embodiment. In some embodiments, the produced workpieces have an improved transmission for electromagnetic radiation in the infrared and/or ultraviolet range.

EXAMPLES

Embodiments will be further clarified below on the basis of examples, but which are not to be considered to be limiting. It will be clear to the person of skill in the art that, instead of the features described herein, other equivalent means can be used in a similar way.

Figure 1:
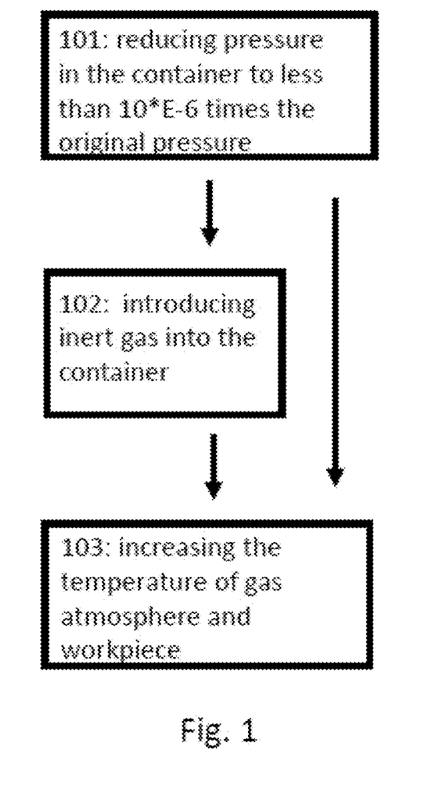
FIG. 1 illustrates a process according to one embodiment.

FIG. 1 illustrates a process according to one embodiment in an exemplary manner. In a first step 101, the partial pressure of atmospheric air is reduced to less than $10^{-6}$-times the original pressure in the container, in which the ceramic material to be sintered is located. For the most part, the original pressure is approximately 1 atm. The total pressure of the atmosphere thereby also decreases in the container, in which the sintering of a workpiece takes place later, which includes a ceramic material. In an optional $2^{nd}$ step 102, a protective gas can optionally be admitted into the container. The protective gas can be, for example, argon. For example, the original total pressure can be established thereby, for example to approximately 1 atm. In this case, however, the partial pressure or the original, atmospheric air is still also less than $10^{-6}$-times the original pressure. In this case, the gas atmosphere consists essentially of the admitted protective gas. In a $3^{rd}$ step 103, the gas atmosphere, which surrounds the ceramic material, is brought to an increased temperature, for example at least 1000° C. The ceramic material is thereby sintered in the above-described controlled gas atmosphere.

Figure 2:
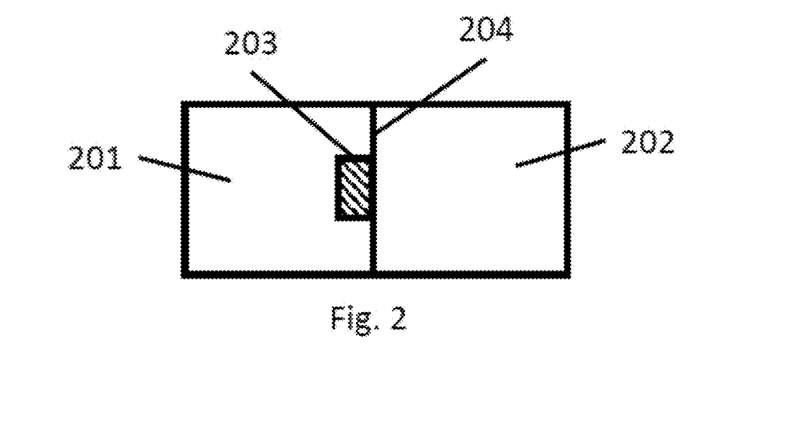
FIG. 2 illustrates a workpiece created by using a sintering process according to one embodiment.

The sintering in this controlled gas atmosphere can reduce or completely or essentially completely prevent, for example, the formation of cracks in the sintered workpiece. FIG. 2 illustrates a workpiece created by using a sintering process. The workpiece can include, for example, a ceramic material 201 and a cermet 202. Cracks 203 can appear at the boundary surface 204 between the ceramic material 201 and the cermet 202 when the gas atmosphere during the sintering of the ceramic material consists of ordinary room air at normal pressure.

Figure 3:
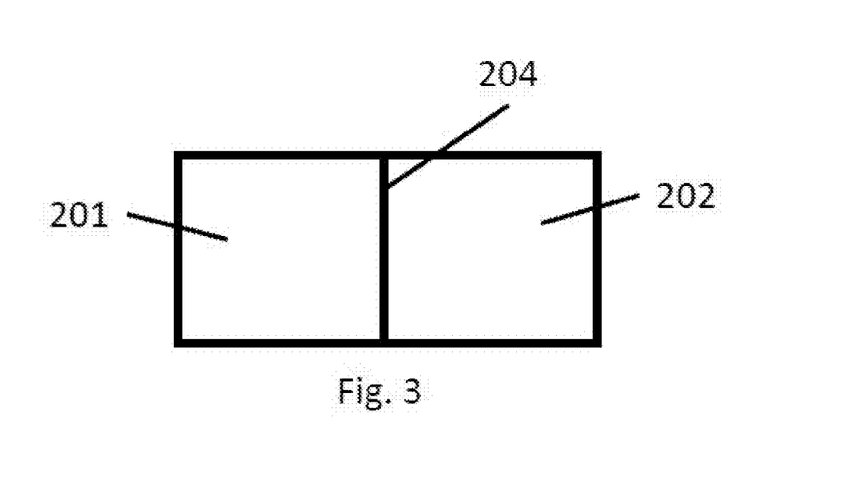
FIG. 3 illustrates a workpiece produced according to the process according to one embodiment.

The process described herein, in the case of which a ceramic material is sintered in a controlled gas atmosphere, can reduce or prevent the appearance of cracks 203. FIG. 3 illustrates a workpiece produced according to the process according to one embodiment. This workpiece includes, for example, no or essentially no cracks 203. When the workpiece includes a cermet 202, the workpiece includes, for example, no or essentially no cracks 203 at the boundary surface 204 between the ceramic material 201 and the cermet 202.

Example 1: Production of Electrical Feedthroughs on the Basis of Cermet

Preparation of Ceramic Green Body Films

Ceramic green body films were used as ceramic precursors for the insulating base body. 99.7% by weight of pure $Al_2O_3$ films (Keral 99 by Keramische Folien GmbH) with a thickness of 400 µm were used for this purpose. Samples of the green body films were trimmed to 90 mm×90 mm squares. Approximately circular holes with a diameter of 400 µm were punched by using a mechanical punch (CPC923101 by Groz-Beckert KG) for a 400 µm diameter in an automated punching machine (MP4150 punching machine by Unichem Industries Inc.) into the film samples. At least 4 film samples were prepared in this way.

Filling

The holes prepared in the above manner were filled with cermet paste using a stencil (Christian Koenen GmbH) and a screen printer (model: M2H, EKRA Automatisierungssysteme GmbH).

For the cermet paste, 60 g of a platinum powder were mixed with 24 g of an $Al_2O_3$ powder by using an organic binding agent on the basis of ethyl cellulose, and were homogenized by using a 3-roller mill. Pastes obtained in this way had viscosities in a range of from 250 to 300 Pa*s (measured by using a Haake Rheostress 6000 rheometer at 25° C.) and a fineness of grind (fog) of less than 10 µm. The rheology of the pastes was suitable for the subsequent stencil printing.

The thickness of the stencil was 100 µm. The openings of the stencil had the same dimensions and positions as the holes, which had been punched into the green body film as above. The pressure parameters were 50 N of squeegee pressure, squeegee speed forwards of 25 mm/s, squeegee speed backwards of 25 mm/s, and snap off of 0.0 mm. 10 minutes after the filling of the samples, they were introduced into a dryer HHG-2 (BTU International Inc.) and were dried there for 10 minutes at 80° C.

A filling of a thickness of approximately 200 µm was obtained after the printing (wet) and of approximately 150 µm after the drying. To completely fill the hole of the film, further filling steps were performed with the cermet paste. 1 to 5 film samples were completely filled with the cermet paste by performing the above filling step several times.

Laminating the Green Body Films 4 layers of green body film comprising holes, which are filled in the above manner, are stacked by using a metal alignment tool and are isostatically pressed in an oil bath at 70° C. with a pressure of 350 bar for 10 minutes (Laminator-CE-1 by Autoclave Engineers), in order to obtain the desired component thickness of 1.6 mm prior to the sintering.

Sintering

The laminate of green body films obtained in the above manner was fired in a high-temperature chamber furnace (FHT-175-10-12 by the Arnold Schröder Industriehöfen GmbH), suitable for a maximum temperature of 1750° C. with a chamber size of 200 mm×250 mm×200 mm, in order to sinter the individual layers and cermet fillings. The sintering process took place under different atmospheric conditions: (1) normal room air at normal pressure (1 atm), (2) pure argon atmosphere, (3) normal room air at reduced pressure ($10^{-6}$ atm). The debinding of the laminate was carried out under normal room air. For this purpose, the temperature was increased from 25 to 450° C. at a rate of 90 K/h. The temperature was subsequently increased to a maximum temperature in a range of from 1600 to 1750° C. at a rate of 450 K/h under the above-mentioned different atmospheric conditions, and was kept constant at this value for a holding time in a range of from 1 to 5 hours, for example 3 hours. The temperature was then lowered to room temperature at a cooling rate of 450° C./h or the natural cooling rate, which was slower. Further samples were sintered in an isostatic press at 2000 bar and 1650° C. in normal room air (4).

Sintered shaped bodies with a volume fraction of 40% by volume to 45% by volume of platinum in the cermet were obtained.

Aftertreatment

After the firing, the samples were ground down and were trimmed to the desired dimensions by using a laser.

The sintered samples were ground on both sides to a thickness of from 1.0 to 1.1 mm.

Measuring the Tightness by Using a Helium Leak Test

Figure 4:
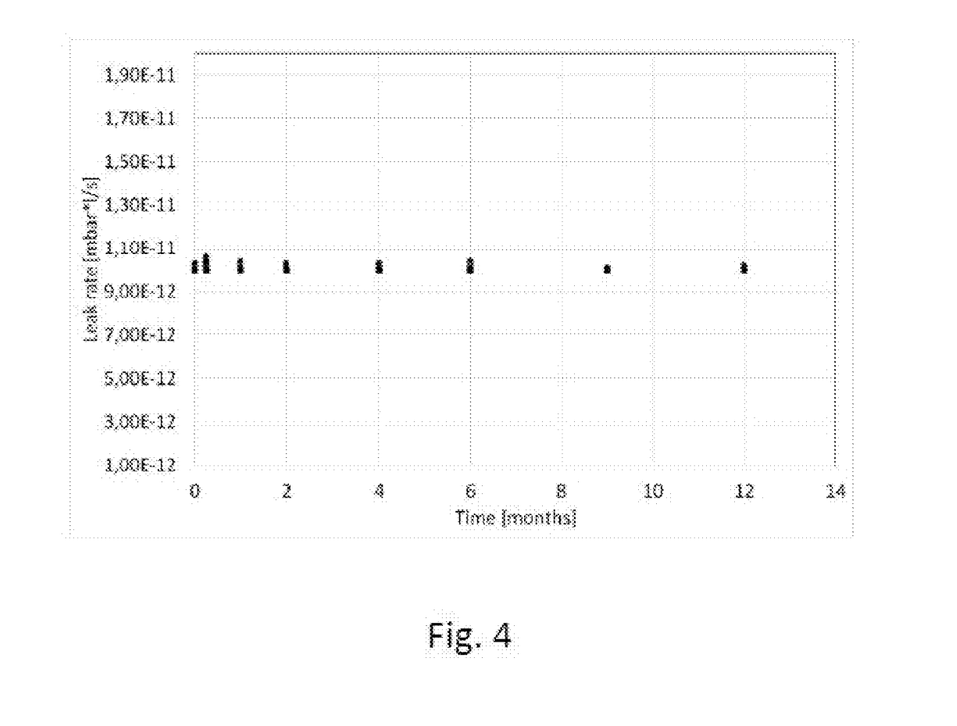
FIG. 4 illustrates helium leak rate for samples according to one embodiment.

The different samples were measured according to the "MIL-STD-883K w/Change 3, METHOD 1014.17 test condition A4" standard. Prior to the leak test, it was ensured that the components were clean and free from residual moisture. The results are shown in Tab. 1. FIG. 4 furthermore illustrates that all 16 of the measured samples, which were sintered under vacuum, still have a helium leak rate of less than $1.1 \times 10^{-11}$ mbar*L/s even twelve months after their production.

Measuring the Porosity

Figure 5A:
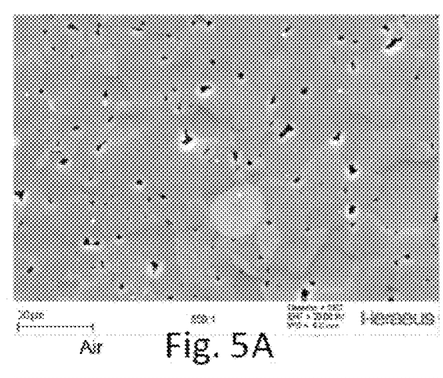
FIGS. 5A-5D illustrate electron microscope pictures of samples in accordance with various embodiments.
Figure 5B:
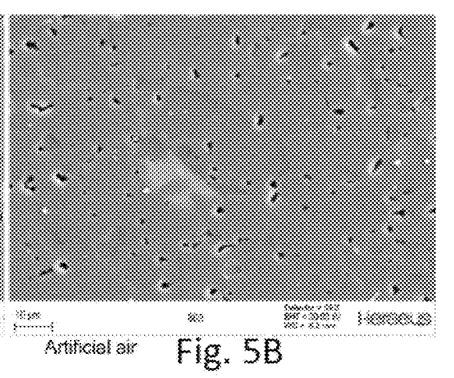
Figure 5C:
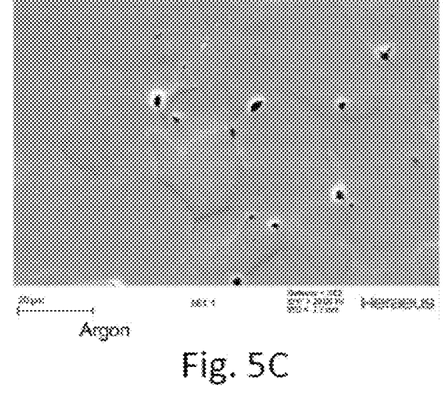
Figure 5D:
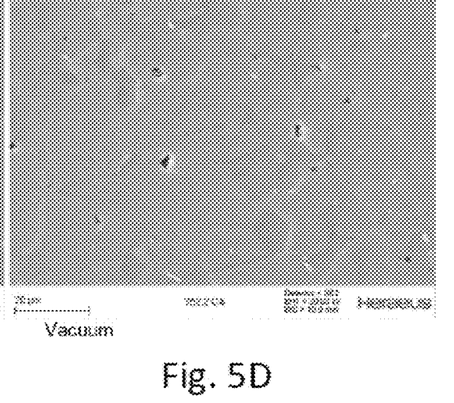

To measure the porosity, metallographic samples were produced by embedding into epoxy resin, grinding by using SiC paper with successively smaller grain size, as well as polishing with a diamond paste. Pictures of the sample surface treated in this way were then taken by using an electron microscope (Zeiss Ultra 55, Carl Zeiss AG). The highest possible contrast between the pores of the sample and the material (ceramic) is to be attained thereby. To evaluate the images, these greyscale images were converted into binary images by using the Otsu method. This means that the image pixels were in each case assigned to a pore or the sample material by using a threshold value. Based on the binary images, the porosity was subsequently determined as quotient from the number of the pixels, which represent pores, and the total number of the pixels per image. The porosity was thereby determined as arithmetic average value from 5 images, each taken at 5 samples. The results are shown in Tab. 1. The electron microscope pictures shown in FIG. 5 make it clear that samples sintered at normal pressure in room air (FIG. 5A) or artificial air (FIG. 5B) have a significantly higher porosity than the samples sintered under argon atmosphere (FIG. 5C) or vacuum (FIG. 5D).

The porosity of a sample represents the ratio of cavity volume of the sample to the total volume of the sample. A sample with a total volume of 1 mm$^3$ and a cavity volume of 0.15 mm$^3$ has a porosity of, for example, 15%. The percentage of the porosity is an indication in percent by volume (vol.-%).

Determination of the Grain Size

The grain size of the purely ceramic portion of the sintered samples is determined based on a metallographic grinding pattern obtained according to the above method according to the linear intercept method. Line patterns are used thereby, and the grain size is determined on the basis of the average cut length. The procedure is performed according to EN 623-3:2003. The grain size used herein is thus identical to the average grain size, which is measured in the standard and which is determined from the cut line length. The scanning electron microscope Zeiss Ultra 55 (Carl Zeiss AG) is furthermore used for the measurement. According to point 7.3 of the standard, microstructure pictures of 3 different regions of the sample are made for each measurement. In the case of the applicability of the process A (criteria see standard), one furthermore proceeds according to the first alternative under point 8.2 of the standard. The results are shown in Tab. 1.

Although specific embodiments have been illustrated and described herein, it will be appreciated by those of ordinary skill in the art that a variety of alternate and/or equivalent implementations may be substituted for the specific embodiments shown and described without departing from the scope of the present embodiment. This application is intended to cover any adaptations or variations of the specific embodiments discussed herein. Therefore, it is intended that this embodiment be limited only by the claims and the equivalents thereof.

The invention claimed is:

1. A process for producing a sintered workpiece, comprising pre-sintering of a ceramic material at a temperature of more than 1000° C. and less than 1600° C. for 1 hour, then further sintering of the ceramic material maximally for 1 hour at a temperature of more than 1600° C. and in an atmosphere, in the case of which the partial pressure of atmospheric air is reduced to less than $10^{-6}$-times, based on the ambient air at the same temperature under equilibrium conditions, wherein the ceramic material comprises a metal oxide selected from a group consisting of alumina ($Al_2O_3$), magnesia (MgO), zirconia ($ZrO_2$), aluminum titanate ($Al_2TiO_5$), and piezoceramics, or a combination thereof, wherein the ceramic material comprises a cermet, wherein the cermet comprises a precious metal, and wherein the precious metal is selected from a group consisting of platinum, silver, gold, tantalum, molybdenum, and titanium.

2. The process according to claim 1, wherein in the case of which the partial pressure of atmospheric air is reduced to less than $10^{-8}$-times, based on the ambient air at the same temperature under equilibrium conditions.

3. The process according to claim 1, wherein the atmosphere during the sintering has a total pressure of less than 100 Pa.

4. The process according to claim 1, wherein the atmosphere during the sintering has a total pressure of less than 0.001 Pa.

5. The process according to claim 1, wherein the atmosphere during the sintering has a partial oxygen pressure of less than 1 Pa.

6. The process according to claim 1, wherein the atmosphere during the sintering has a partial oxygen pressure of less than 0.001 Pa.

7. The process according to claim 1, wherein the atmosphere during the sintering has a partial water pressure of less than 1 Pa.

TABLE 1

Results of the helium leak test and the porosity measurements from example 1.

| Sintering condition | Helium leak rate [mbar*l/s] | Porosity | Appearance of the sample | Grain size |
|---|---|---|---|---|
| (1) room air | $10^{-3}$-$10^{-4}$ | 1.76% | ivory-colored, opaque, cracks in the edge region of the vias | smaller than 20 μm |
| (2) pure argon atmosphere | $10^{-11}$ | 0.56% | grey-white, transparent | larger than 20 μm |
| (3) normal room air at reduced pressure ($10^{-6}$ atm) | $10^{-11}$ | 0.39% | grey-white, transparent | larger than 20 μm |
| (4) isostatic pressing at 2000 bar and 1650° C. | $10^{-3}$ | not determined | not determined | not determined |

8. The process according to claim 1, wherein the atmosphere during the sintering has a partial water pressure of less than 0.001 Pa.

9. The process according to claim 1, wherein the atmosphere comprises a protective gas, selected from a group consisting of argon, nitrogen, helium, or a combination thereof.

10. The process according to claim 1, wherein the workpiece is configured for installation in an implantable medical product, wherein the medical product is selected from a group consisting of a pulse generator, pacemaker, cardiac resynchronization device, actuator, sensor, and stimulator.

11. The process according to claim 1, wherein pre-sintering of the ceramic material is at a temperature of more than 1000° C. and less than 1100° C.

12. The process according to claim 1, wherein pre-sintering of the ceramic material is at ordinary room atmospheric pressure.

* * * * *